(12) United States Patent
Leimkühler et al.

(10) Patent No.: US 6,838,578 B2
(45) Date of Patent: Jan. 4, 2005

(54) PROCESS FOR PREPARING (CYCLO) ALIPHATIC ISOCYANATES

(75) Inventors: Hans-Joachim Leimkühler, Leverkusen (DE); Herbert Stutz, Dormagen (DE); Wolfgang Leuckel, Dürkheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 273 days.

(21) Appl. No.: 10/190,265

(22) Filed: Jul. 3, 2002

(65) Prior Publication Data

US 2003/0013909 A1 Jan. 16, 2003

(30) Foreign Application Priority Data

Jul. 11, 2001 (DE) .......................................... 101 33 729

(51) Int. Cl.$^7$ ............................................. C07C 249/00
(52) U.S. Cl. ...................................................... 560/330
(58) Field of Search .................................. 560/330, 338

(56) References Cited

U.S. PATENT DOCUMENTS

| | | | |
|---|---|---|---|
| 4,847,408 A | 7/1989 | Frosch et al. | 560/347 |
| 5,117,048 A | 5/1992 | Zaby et al. | 560/347 |
| 5,391,683 A | 2/1995 | Joulak et al. | 528/57 |
| 5,633,396 A | 5/1997 | Bischof et al. | 560/347 |
| 6,225,497 B1 | 5/2001 | Becker et al. | 560/347 |

FOREIGN PATENT DOCUMENTS

| | | |
|---|---|---|
| EP | 0 676 393 | 10/1995 |
| SU | 407567 | 12/1973 |

*Primary Examiner*—Paul J. Killos
(74) *Attorney, Agent, or Firm*—Joseph C. Gil; Thomas W. Roy; Gary F. Matz

(57) ABSTRACT

The present invention relates to a process for preparing (cyclo)aliphatic diisocyanates and triisocyanates corresponding to the formula $$R-(NCO)_n \qquad (I),$$

wherein

R represents a (cyclo)aliphatic hydrocarbon group having up to 15 carbon atoms, provided that there are at least two carbon atoms between two nitrogens, n represents the number 2 or 3, by a) separately heating phosgene and a diamine or triamine corresponding to the formula $$R-(NH_2)_n \qquad (II),$$

to a temperature of 200° C. to 600° C., wherein the amine may optionally be diluted with an inert gas or with the vapors of an inert solvent, b) optionally passing the reactants over torque-producing baffles and c) continuously reacting phosgene and the amine in the gas phase in a reaction chamber without moving parts and with constrictions of the walls in the region of the reaction zone.

10 Claims, 1 Drawing Sheet

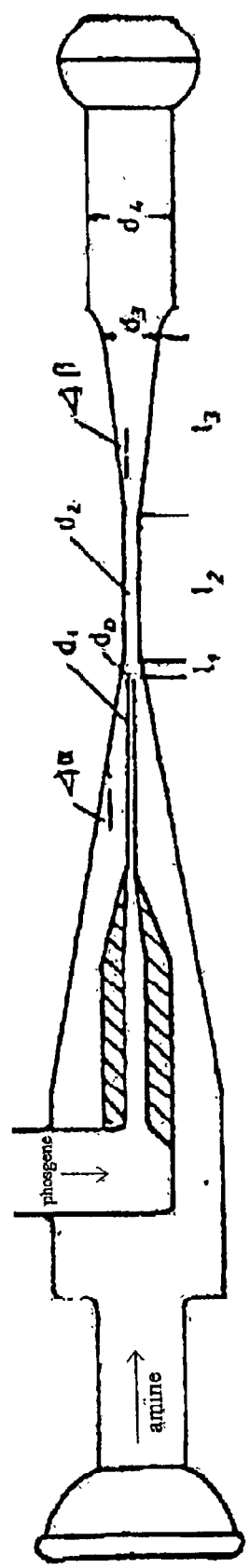
FIGURE

PROCESS FOR PREPARING (CYCLO) ALIPHATIC ISOCYANATES

FIELD OF THE INVENTION

The present invention relates to a process for preparing (cyclo)aliphatic diisocyanates and triisocyanates by the phosgenation of (cyclo)aliphatic diamines and triamines in the gas phase using special reactors.

BACKGROUND OF THE INVENTION

It is known that (cyclo)aliphatic diamines can be phosgenated in the gas phase. In SU-A 00 407 567 the reactor used for this purpose is heated on the outside and on the inside and provided with cooling coils in order to remove the heat of reaction. On the inside of this reactor is a holder for the preheating units around which are arranged pipes through which the reactants are passed. The reactor itself also has external heaters. The preheaters and the external heaters are switched on until the temperature reaches 210° C. to 230° C. A stoichiometric quantity of phosgene is then passed through one pipe, while the gaseous or liquid amine reaches the reactor via the other pipe. The reactor has previously been heated to a temperature of 30° C. to 60° C. above the boiling temperature of the amine. Gaseous isocyanate is then formed in the reactor. The heat of reaction is removed through cooling coils. When the latter have become sufficiently hot, the heater is switched off. The external heater is switched on only if this is necessary in order to compensate for heat losses, so that the product does not cool to below 210° C. to 230° C. The gaseous products leave the reactor through an outlet. The disadvantage of this reactor is that it is suitable only for batch operation.

In GB-A 1 165 831, the reaction is carried out in a tubular reactor equipped with a mechanical stirrer. The reactor resembles a film evaporator in which the stirrer mixes the gases and at the same time brushes over the heated walls of the tubular reactor, in order to prevent a build-up of polymeric material on the wall of the pipe. However, the use of a high-speed stirrer when handling phosgene at a temperature of approximately 300° C. necessitates great expense on safety measures to seal the reactor and retain the stirrer in the highly corrosive medium.

EP-A 0 289 840 and EP-A 0 749 958 describe a cylindrical reaction chamber without moving parts, in which the reactants are reacted with one another while a turbulent flow is maintained. The geometrical form of the cylindrical reaction chamber leads to back-mixing processes, as a result of which the products react with the diamine starting material to form solid deposits. This leads to contamination of the reactor and blockages in the path of the gas.

The phosgenation of aromatic diamines is described in EP-A 0 593 334 in which the reactants are initially mixed in a turbulent flow (at Reynolds numbers of at least 3000, preferably at least 8000). The reaction is then carried out under laminar or turbulent flow conditions in a tubular reactor without movable mixing elements and with a constriction of the walls. The fact that it is possible to phosgenate aromatic diamines cannot automatically be transferred to aliphatic or cycloaliphatic diamines or triamines because the corresponding reactions differ fundamentally from one another with regard to mechanism, solid-forming secondary reactions and required reaction times.

It is an object of the present invention to produce (cyclo) aliphatic isocyanates by the gas-phase phosgenation of the corresponding amines while avoiding the previously mentioned disadvantages of prior art.

This object may be achieved with the process of the present invention by carrying out the reaction in a reactor which differs from the prior art cylindrical form in a specific way, which is described below.

SUMMARY OF THE PRESENT INVENTION

The present invention relates to a process for preparing a (cyclo)aliphatic diisocyanate or triisocyanate corresponding to the formula $$R\text{—}(NCO)_n \qquad (I),$$

wherein

R represents a (cyclo)aliphatic hydrocarbon group having up to 15 carbon atoms, provided that there are at least two carbon atoms between two nitrogens, n represents the number 2 or 3, by a) separately heating phosgene and a diamine or triamine corresponding to the formula $$R\text{—}(NH_2)_n \qquad (II),$$

to a temperature of 200° C. to 600° C., wherein the diamine or triamine may optionally be diluted with an inert gas or with the vapors of an inert solvent, b) optionally passing the reactants over torque-producing baffles and c) continuously reacting phosgene and the diamine or triamine in the gas phase in a reaction chamber without moving parts and with constrictions of the walls in the region of the reaction zone.

BRIEF DESCRIPTION OF THE DRAWING

The FIGURE shows one embodiment of the reaction chamber according to the invention with constrictions of the walls in the reaction zone.

DETAILED DESCRIPTION OF THE INVENTION

Starting materials for the process according to the invention are (cyclo)aliphatic diamines or triamines corresponding to the formula $$R\text{—}(NH_2)_n \qquad (II),$$

wherein

R represents a (cyclo)aliphatic hydrocarbon group having up to 15 carbon atoms, preferably 4 to 13 carbon atoms, provided that there are at least two carbon atoms between two amino groups, n represents the number 2 or 3.

Examples of suitable (cyclo)aliphatic diamines include 1,4-diaminobutane, 1,6-diaminohexane, 1,11-diaminoundecane, 1,4-diaminocyclohexane, 1-amino-3,3,5-trimethyl-5-aminomethylcyclohexane (IPDA), 4,4'-diaminodicyclohexylmethane and 4,4'-diaminodicyclohexyl-propane-(2,2). An example of a suitable (cyclo)aliphatic triamine is 1,8-diamino-4-(aminomethyl)octane, triaminononane. Preferred starting amines are 1,6-diaminohexane, IPDA, 4,4'-diaminodicyclohexylmethane and triaminononane.

The products obtained from the phosgenation reaction are (cyclo)aliphatic diisocyanates or (cyclo)aliphatic triisocyanates corresponding to formula (I)

$$R\text{—}(NCO)_n \qquad (I),$$

wherein

R represents a (cyclo)aliphatic hydrocarbon group having up to 15 carbon atoms, preferably 4 to 13 carbon atoms, provided that there are at least two carbon atoms between two isocyanate groups,
n represents the number 2 or 3.

Preferred diisocyanates are 1,6-diisocyanatohexane, 1-isocyanato-3,3,5-trimethyl-5-isocyanatomethylcyclohexane (IPDI) and 4,4'-diaminodicyclohexylmethane. A preferred triisocyanate is 1,8-diisocyanato-4-(isocyanatomethyl)octane or triisocyanatononane.

Before the process according to the invention is carried out, the starting amines are vaporized and heated to 200° C. to 600° C., preferably 250° C. to 500° C., and passed to the reactor, optionally diluted with an inert gas (for example, $N_2$ or argon) and/or with the vapors of an inert solvent (for example, dichlorobenzene).

Before the process according to the invention is carried out, the phosgene used for the phosgenation reaction is heated to a temperature of 200° C. to 600° C., preferably 250° C. to 500° C.

Shortly before being mixed in the reactor, both reactants may be passed over torque-producing baffles in order to stabilize the flow.

To carry out the process according to the invention, the preheated and optionally torque-laden flows of the diamine or diamine-inert gas mixture and phosgene are passed continuously into a reaction chamber without moving parts, with constrictions of the walls, and mixed together. The size of the apparatus used depends upon the quantity of product to be produced.

Suitable reaction chambers have, for example, an abrupt widening of the cross-sectional area at an angle of 80° to 90°, preferably 90°, in the direction of flow after the mixing of the two educts. Here the ratio of the cross-sectional areas of the reaction chamber after and before the widening is 3:1 to 7:1, preferably 4.5:1 to 5.5:1. Eddies, which keep the main flow away from the reactor wall, may develop at this widening point. This shape can consequently decrease the contact of the reaction zone with the container wall. The polymerizable products are thereby kept away from the reactor wall and the formation of solid deposits and possible contamination are thus decreased.

Another suitable embodiment of the reaction chamber according to the invention has a cascade-like and/or continuous variation in the cross-sectional area. In this way the flow rate of the reaction mixture along the axis of the reactor can be adjusted. A narrowing of the cross-section or preferably a slight widening up to twice, preferably up to 1.5 times, the initial cross-section, as a result of the enlargement in volume leads to an acceleration of the flow during the reaction. This stabilizes the flow and counteracts the risk of back flows. The flow rate of the reaction mixture can be maintained exactly constant along the length of the reactor by a suitably chosen widening of the cross-sectional area. In this way the available reaction time is increased, with the same length of reactor.

The reactors are preferably prepared from steel, glass, or alloyed or enamelled steel and are a sufficient length to facilitate a complete reaction of the amine with phosgene under the process conditions. The gas flows are generally introduced into the reaction chamber at one end. This introduction can be effected, for example, through nozzles attached to one end of the reactor, or through a combination of nozzle and annular gap between nozzle and wall. The mixing zone is also maintained at a temperature of 200° C. to 600° C., preferably 250° C. to 500° C. This temperature is maintained, if necessary, by heating the reactor.

While the process according to the invention is being carried out, the pressure is preferably 200 mbar to 3000 mbar within the feed pipes to the reaction chamber and 150 mbar to 2000 mbar at the outlet of the reaction chamber. The flow rate within the reaction chamber is at least 3 m/s, preferably at least 6 m/s and most preferably 10 m/s to 120 m/s and is maintained by a suitable pressure differential. Under these conditions, turbulent flows generally prevail within the reaction chamber.

An advantage of the process according to the invention is that a reactor having a higher space-time yield is attained, together with an equal or better quality of product. The useful life of the reactor (i.e., the production time in relation to idle times, which are necessary for the cleaning of the reactor) can be increased by 40% to 60%, depending upon the isocyanate produced.

The invention is further illustrated but is not intended to be limited by the following examples in which all parts and percentages are by weight unless otherwise specified.

EXAMPLE

The process according to the invention is explained in more detail by the following Example.

Into a mixing tube with a downstream diisocyanate condensation step and a phosgene adsorption tower filled with activated carbon, 5.91 mol/h of phosgene, which had been heated to a temperature of 400° C. at a pressure of 1100 mbar in an upstream heat exchanger, flowed continuously through a nozzle with an external diameter $d_1$ of 1.7 mm and an internal diameter $d_0$ of 1.0 mm, which projected into the mixing tube. At the same time, a mixture of 1.26 moles of gaseous hexamethylene-diamine and 1.25 moles of nitrogen, heated to 400° C., was passed hourly into the mixing tube through the annular gap between nozzle and mixing tube. The diameter of the mixing tube varied along the longitudinal axis by decreasing down to a diameter $d_2$ of 2.5 mm, at an angle α of 10°, upstream of the nozzle and up to 1.5 mm downstream of the nozzle as shown by length $l_1$ in the FIGURE, and then remaining constant along length $l_2$, which had a length of 17.5 mm. Over the 20 mm length $l_3$ the diameter increased at an angle β of 5° until the diameter $d_3$ was 6.0 mm. The diameter then increased to 10.0 mm as shown by diameter $d_4$. A pressure of approximately 350 mbar was maintained in the mixing tube by applying a vacuum to the outlet from the phosgene adsorption tower. In a condensation step, the hot reaction mixture leaving the reaction chamber was passed through dichlorobenzene, which was maintained at a temperature of 150° C. to 160° C. A selective condensation of diisocyanatohexane took place. The gas mixture, which substantially contained nitrogen, hydrogen chloride and excess phosgene, was passed through the washing step and subsequently freed from phosgene in the adsorption tower. The diisocyanate was recovered in pure form from the washing solution by distillation. The yield of 1,6-diisocyanatohexane was 98.0% of the theoretical yield.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a (cyclo)aliphatic diisocyanate or triisocyanate corresponding to the formula

  (I), wherein
R represents a (cyclo)aliphatic hydrocarbon group having up to 15 carbon atoms, provided that there are at least two carbon atoms between two nitrogens,
n represents the number 2 or 3,
which comprises
a) separately heating phosgene and a diamine or triamine corresponding to the formula

  (II), to a temperature of 200° C. to 600° C., wherein the amine may optionally be diluted with an inert gas or with the vapors of an inert solvent,
b) optionally passing the reactants over torque-producing baffles and
c) continuously reacting phosgene and the amine in the gas phase in a reaction chamber without moving parts and with constrictions of the wall in the region of the reaction zone, wherein the reaction chamber has an abrupt widening of the cross-sectional area in the direction of flow after the mixing of the reactants.

2. The process of claim 1 wherein the reaction chamber has a cascade-like and/or continuous variation in the cross-sectional area.

3. The process of claim 1 wherein the cross-sectional area of the reaction chamber widens at an angle of 80° to 90° and wherein the ratio of the cross-sectional areas of the reaction chamber before and after the widening is 3:1 to 7:1.

4. The process of claim 2 wherein the cross-sectional area of the reaction chamber widens continuously or cascade-like and the ratio of the cross-sectional areas of the reaction chamber before and after the widening is greater than 1:1 to 2:1.

5. The process of claim 1 which comprises passing the phosgene and amine over torque-producing baffles shortly before being mixed in the reactor.

6. The process of claim 1 wherein said amine is diluted with an inert gas and/or with the vapors of an inert solvent.

7. The process of claim 1 wherein said diamine comprises 1,6-diaminohexane.

8. The process of claim 1 wherein the diisocyanate comprises 1,6-diisocyanatohexane.

9. The process of claim 1 wherein the triamine comprises triaminononane.

10. The process of claim 1 wherein the triisocyanate comprises triisocyanatononane.

* * * * *